(12) United States Patent
Highsmith

(10) Patent No.: US 12,178,500 B2
(45) Date of Patent: Dec. 31, 2024

(54) MAPPING CATHETER WITH FLEX PANEL ELECTRODE ASSEMBLY

(71) Applicant: Biosense Webster (Israel) Ltd., Yokneam (IL)

(72) Inventor: Debby E. Highsmith, Laguna Niguel, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 401 days.

(21) Appl. No.: 16/942,825

(22) Filed: Jul. 30, 2020

(65) Prior Publication Data

US 2021/0059745 A1 Mar. 4, 2021

Related U.S. Application Data

(60) Provisional application No. 62/895,193, filed on Sep. 3, 2019.

(51) Int. Cl.
*A61B 18/14* (2006.01)
*A61B 5/287* (2021.01)
(Continued)

(52) U.S. Cl.
CPC .......... *A61B 18/1492* (2013.01); *A61B 5/287* (2021.01); *A61B 2018/00059* (2013.01);
(Continued)

(58) Field of Classification Search
CPC ...... A61B 18/1492; A61B 2018/00059; A61B 2018/00214; A61B 2018/00577;
(Continued)

(56) References Cited

U.S. PATENT DOCUMENTS 5,738,096 A 4/1998 Ben-Haim
5,846,196 A * 12/1998 Siekmeyer ........... A61B 5/6853
606/41

(Continued)

FOREIGN PATENT DOCUMENTS

JP 2017-070750 A 4/2017

OTHER PUBLICATIONS

International Search Report and Written Opinion dated Dec. 11, 2020, for International Application No. PCT/IB2020/058084, 12 pages.

(Continued)

*Primary Examiner* — Thomas A Giuliani
*Assistant Examiner* — Abigail M Ziegler
(74) *Attorney, Agent, or Firm* — Frost Brown Todd LLP

(57) ABSTRACT

An apparatus includes a catheter assembly and an end effector. The catheter assembly includes an outer sheath with a distal end. The end effector is associated with a distal end of the catheter assembly. The end effector includes a panel assembly with microelectrodes for electrophysiological (EP) mapping. The microelectrodes are configured in a matrix within the panel assembly and provide multiple points of contact with the target tissue for EP mapping. The panel assembly can transition between a first contracted state and a second expanded state. The panel assembly can fit within the outer sheath in the first state. The panel assembly can expand outwardly away from a longitudinal axis defined by the catheter assembly in the second state once exposed distally relative to the distal end of the outer sheath.

19 Claims, 5 Drawing Sheets

(51) Int. Cl.
  *A61B 18/00* (2006.01)
  *A61B 18/12* (2006.01)
(52) U.S. Cl.
  CPC ............. *A61B 2018/0016* (2013.01); *A61B 2018/00214* (2013.01); *A61B 2018/00577* (2013.01); *A61B 2018/126* (2013.01); *A61B 2018/1465* (2013.01); *A61B 2018/1467* (2013.01); *A61B 2018/1475* (2013.01); *A61B 2562/164* (2013.01)
(58) Field of Classification Search
  CPC .......... A61B 2018/00696; A61B 2018/00773; A61B 2018/00916; A61B 2018/126; A61B 2018/1467; A61B 2562/164; A61B 2562/166; A61B 2018/0016; A61B 5/283; A61B 5/287; A61B 5/6852; A61B 5/6859; A61B 5/6874; A61F 2230/0093
  See application file for complete search history.

(56) References Cited

U.S. PATENT DOCUMENTS

| | | | |
|---|---|---|---|
| 8,956,353 B2 | 2/2015 | Govari et al. | |
| 9,314,299 B2 | 4/2016 | Fang | |
| 9,480,416 B2 | 11/2016 | Govari et al. | |
| 9,801,585 B2 | 10/2017 | Shah et al. | |
| 9,820,664 B2 | 11/2017 | Hoitink et al. | |
| 9,907,480 B2 | 3/2018 | Basu et al. | |
| 10,130,420 B2 | 11/2018 | Basu et al. | |
| 10,130,422 B2 | 11/2018 | Ditter | |
| 11,426,111 B2* | 8/2022 | Olson | A61B 5/287 |
| 2008/0228060 A1 | 9/2008 | Tegg | |
| 2010/0324589 A1* | 12/2010 | Carpenter | A61M 25/0015 606/200 |
| 2013/0030426 A1 | 1/2013 | Gallardo et al. | |
| 2014/0058197 A1* | 2/2014 | Salahieh | A61B 1/00082 600/109 |
| 2015/0105645 A1 | 4/2015 | Subramaniam et al. | |
| 2015/0351652 A1* | 12/2015 | Marecki | A61B 18/1492 29/829 |
| 2015/0374252 A1 | 12/2015 | de la Rama et al. | |
| 2017/0100187 A1* | 4/2017 | Basu | A61B 18/02 |
| 2017/0312022 A1 | 11/2017 | Beeckler et al. | |
| 2018/0056038 A1 | 3/2018 | Aujla | |
| 2018/0071017 A1 | 3/2018 | Bar-tal et al. | |
| 2018/0116539 A1 | 5/2018 | Olson et al. | |
| 2018/0360534 A1* | 12/2018 | Teplitsky | A61B 5/02055 |
| 2020/0060569 A1* | 2/2020 | Tegg | A61B 5/063 |
| 2020/0405386 A1* | 12/2020 | Ostroot | A61B 18/1492 |

OTHER PUBLICATIONS

Japanese Notification of Reasons for Refusal dated Mar. 12, 2024, for Application No. 2022-514533, 7 pages.
Chinese First Office Action and Search Report dated Oct. 14, 2024, for Application No. 202080062302.5, 12 pages.

* cited by examiner

MAPPING CATHETER WITH FLEX PANEL ELECTRODE ASSEMBLY

PRIORITY

This application claims priority to U.S. Provisional Pat. App. No. 62/895,193, entitled "Mapping Catheter with Flex Panel Electrode Assembly," filed Sep. 3, 2019, the disclosure of which is incorporated by reference herein in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein in its entirety; U.S. Pub. No. 2017/0312022, entitled "Irrigated Balloon Catheter with Flexible Circuit Electrode Assembly," published Nov. 2, 2017, the disclosure of which is incorporated by reference herein in its entirety; U.S. Pub. No. 2018/0071017, entitled "Ablation Catheter with a Flexible Printed Circuit Board," published Mar. 15, 2018, the disclosure of which is incorporated by reference herein in its entirety; U.S. Pub. No. 2018/0056038, entitled "Catheter with Bipole Electrode Spacer and Related Methods," published Mar. 1, 2018, the disclosure of which is incorporated by reference herein in its entirety; U.S. Pat. No. 10,130,422, entitled "Catheter with Soft Distal Tip for Mapping and Ablating Tubular Region," issued Nov. 20, 2018, the disclosure of which is incorporated by reference herein in its entirety; U.S. Pat. No. 8,956,353, entitled "Electrode Irrigation Using Micro-Jets," issued Feb. 17, 2015, the disclosure of which is incorporated by reference herein in its entirety; and U.S. Pat. No. 9,801,585, entitled "Electrocardiogram Noise Reduction," issued Oct. 31, 2017, the disclosure of which is incorporated by reference herein in its entirety.

Some catheter ablation procedures may be performed after using electrophysiology (EP) mapping to identify tissue regions that should be targeted for ablation. Such EP mapping may include the use of sensing microelectrodes on a catheter (e.g., the same catheter that is used to perform the ablation or a dedicated mapping catheter). Such sensing microelectrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein in its entirety. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein in its entirety; U.S. Pat. No. 10,130,422, entitled "Catheter with Soft Distal Tip for Mapping and Ablating Tubular Region," issued Nov. 20, 2018, the disclosure of which is incorporated by reference herein in its entirety; and U.S. Pub. No. 2018/0056038, entitled "Catheter with Bipole Electrode Spacer and Related Methods," published Mar. 1, 2018, the disclosure of which is incorporated by reference herein in its entirety.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, California. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein in its entirety; and various other references that are cited herein.

While several catheter systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

I. Overview of Exemplary Catheter System

Figure 1:
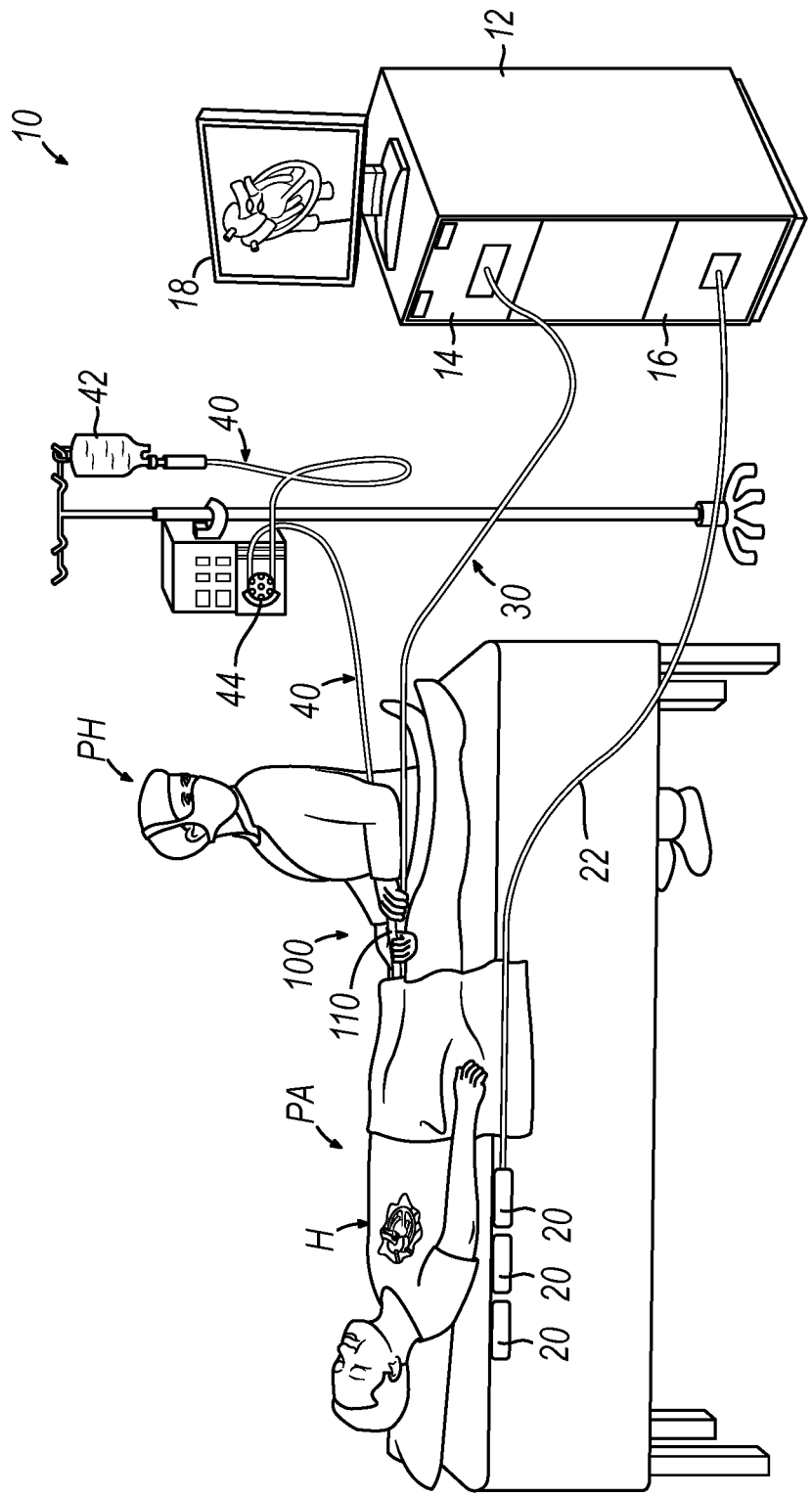
FIG. 1 depicts a schematic view of a medical procedure in which a catheter of a catheter assembly is inserted in a patient.
Figure 2:
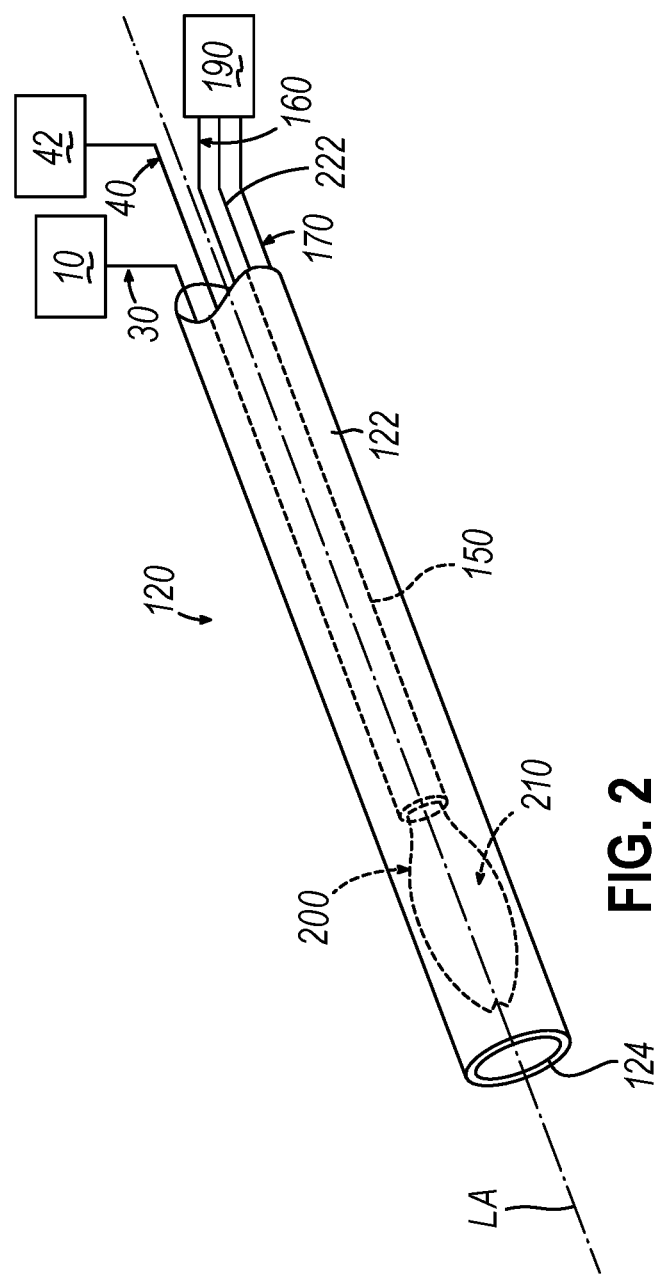
FIG. 2 depicts a perspective view of a distal portion of the catheter of FIG. 1, with an end effector of the catheter in a proximal position relative to an outer sheath of the catheter.
Figure 3:
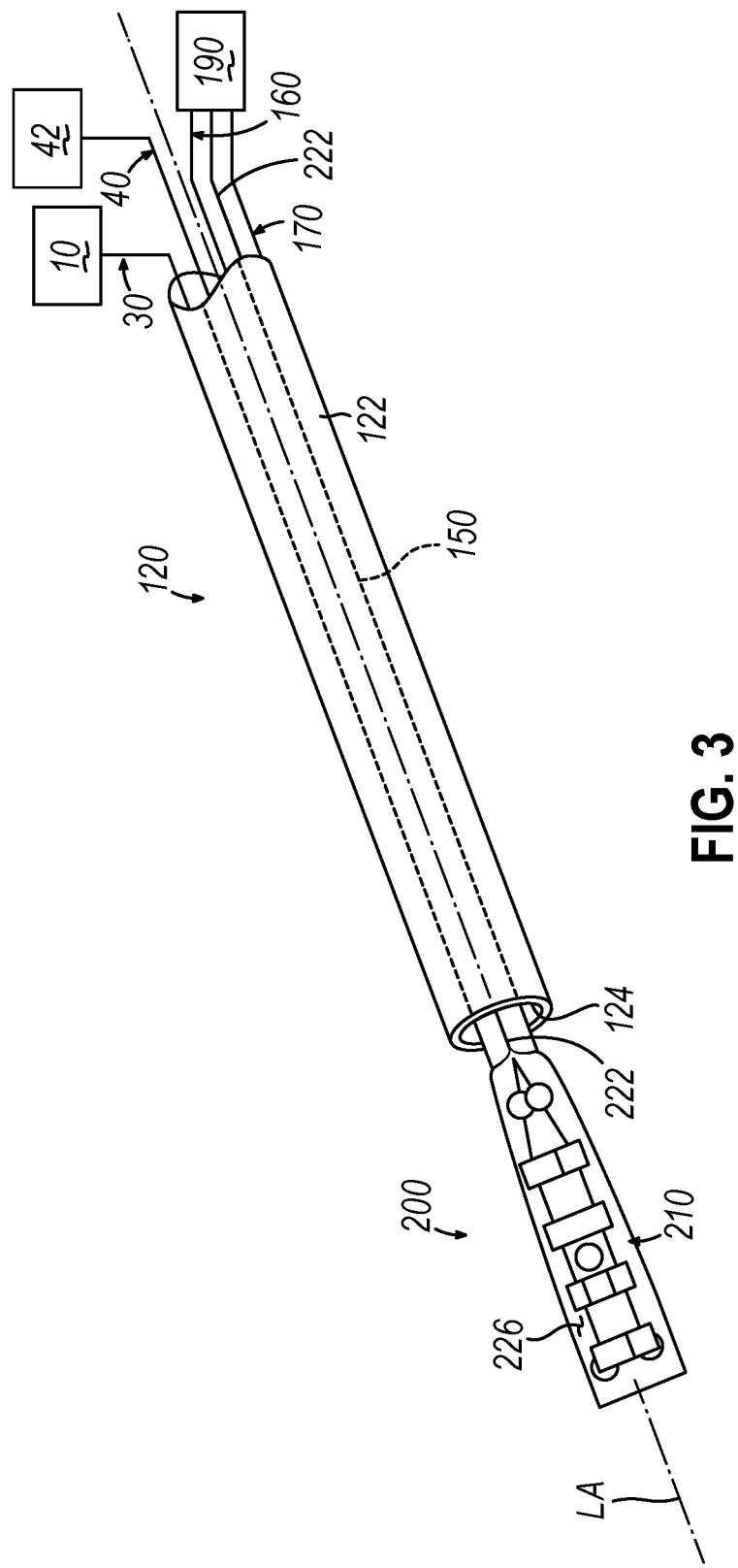
FIG. 3 depicts a perspective view of the distal portion of the catheter of FIG. 2, with the end effector in a distal position relative to the outer sheath of the catheter, and with the end effector in a contracted state.
Figure 4:
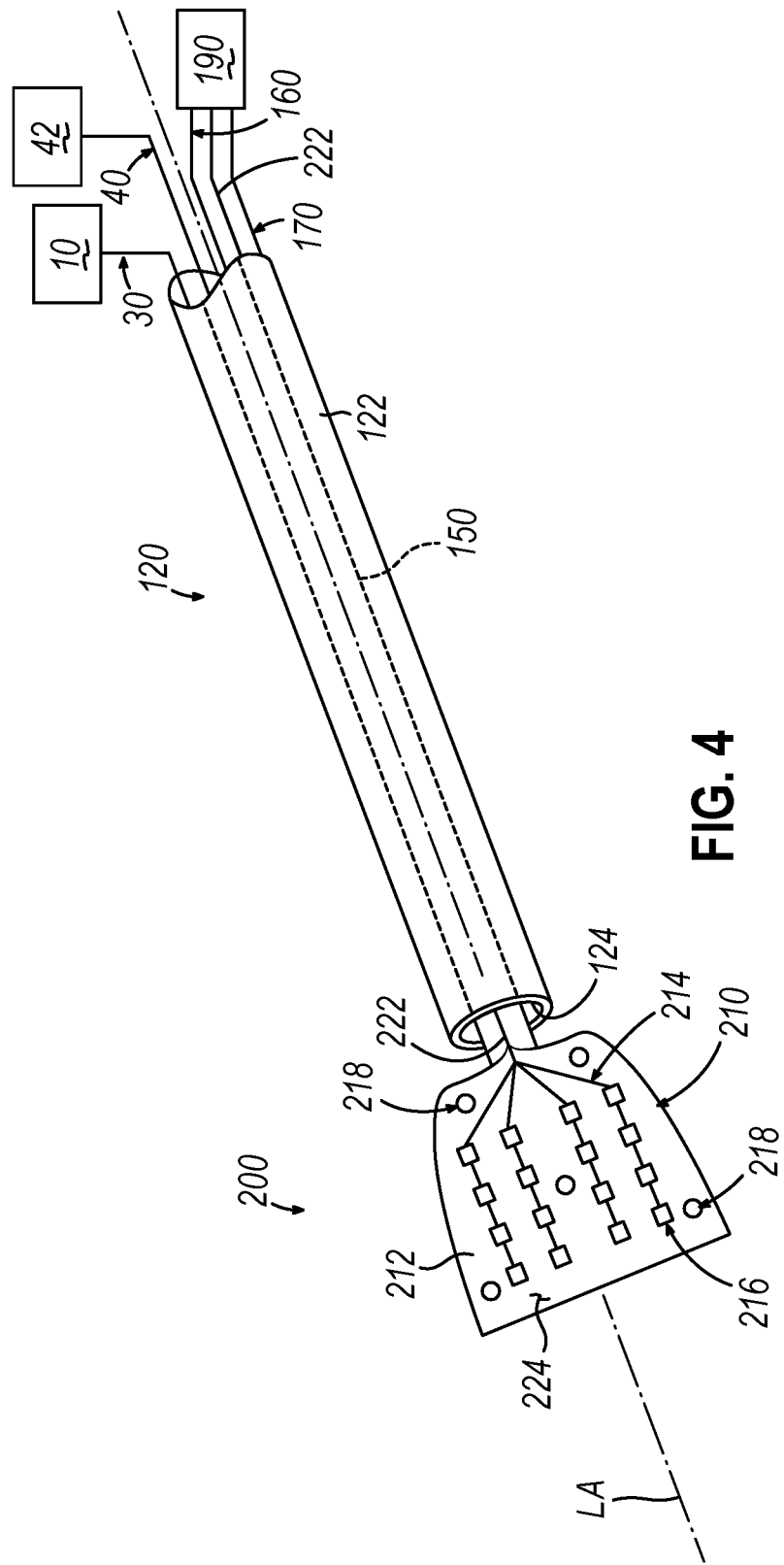
FIG. 4 depicts a perspective view of the distal portion of the catheter of FIG. 3, with the end effector in an expanded state.

FIG. 1 shows an exemplary medical procedure and associated components of a cardiac ablation system. In particular, FIG. 1 shows a physician (PH) grasping a handle (110) of a catheter assembly (100), with an end effector (200) of a flexible catheter (120) (shown in FIGS. 2-4) of catheter assembly (100) disposed in a patient (PA) to map or ablate tissue in or near the heart (H) of the patient (PA). As shown in FIGS. 2-4, catheter (120) includes an outer sheath (122), with end effector (200) being disposed at or near a distal end (124) of outer sheath (122). Catheter assembly (100) is coupled with a guidance and drive system (10) via a cable (30). Catheter assembly (100) is also coupled with a fluid source (42) via a fluid conduit (40), though this is merely optional. A set of field generators (20) are positioned underneath the patient (PA) and are also coupled with guidance and drive system (10) via a cable (22).

Guidance and drive system (10) of the present example includes a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via microelectrodes (216) of end effector (200) as described in greater detail below. Console (12) includes a processor (not shown) that processes such EP mapping signals and thereby provides EP mapping as is known in the art. In addition, or in the alternative, first driver module (14) may be operable to provide RF power to other electrodes of end effector (200) to thereby ablate tissue. In some versions, first driver module (14) is also operable to receive position indicative signals from one or more position sensors in end effector (200), as will be described in greater detail below. In such versions, the processor of console (12) is also operable to process the position indicative signals from the position sensors to thereby determine the position of the end effector (200) of catheter (120) within the patient (PA).

Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

Display (18) is coupled with the processor of console (12) and is operable to render images of patient anatomy. Such images may be based on a set of preoperatively or intraoperatively obtained images (e.g., a CT or MM scan, 3-D map, etc.). The views of patient anatomy provided through display (18) may also change dynamically based on signals from the position sensor of end effector (200). For instance, as end effector (200) of catheter (120) moves within the patient (PA), the corresponding position data from the position sensor may cause the processor of console (12) to update the patient anatomy views in display (18) in real time to depict the regions of patient anatomy around end effector (200) as end effector (200) moves within the patient (PA). Moreover, the processor of console (12) may drive display (18) to show locations of aberrant conductive tissue sites, as detected via EP mapping with end effector (200). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (200) on the images of the patient's anatomy, such as by superimposing an illuminated dot, a crosshair, a graphical representation of end effector (200), or some other form of visual indication. Such a superimposed visual indication may also move within the images of the patient anatomy on display (18) in real time as the physician moves end effector (200) within the patient (PA), thereby providing real-time visual feedback to the operator about the position of end effector (200) within the patient (PA) as end effector (200) moves within the patient (PA). The images provided through display (18) may thus effectively provide a video tracking of the position of end effector (200) within a patient (PA), without necessarily having any optical instrumentation (i.e., cameras) viewing end effector (200). In the same view, display (18) may simultaneously visually indicate the locations of aberrant conductive tissue sites detected through the EP mapping as described herein. The physician (PH) may thus view display (18) to observe the real time positioning of end effector (200) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). In some variations, conduit (40), fluid source (42), and pump (44) are omitted entirely. In versions where these components are included, end effector (200) may be configured to communicate irrigation fluid from fluid source (42) to the target site in the patient. Such irrigation may be provided in accordance with the teachings of any of the various patent references cited herein; or in any other suitable fashion as will be apparent to those skilled in the art in view of the teachings herein.

II. Exemplary End Effector

FIGS. 2-4 show end effector (200) of catheter assembly (100) in greater detail. End effector (200) is mounted to an inner shaft (150), which is internal to outer sheath (122) and is slidably disposed relative to outer sheath (122). As shown, end effector (200) includes a panel assembly (210) that is collapsible to fit within an outer sheath (122). FIG. 2 shows a state in which end effector (200) is retracted proximally relative to outer sheath (122), such that end effector (200) is proximal to distal end (124) of outer sheath (122). In this state, end effector (200) deformably conforms to the cylindraceous interior of outer sheath (122). Catheter (120) and end effector (200) may be in the state shown in FIG. 2 when catheter (120) is introduced into the body of the patient (PA); and during transit from the insertion site to the targeted cardiovascular region within the patient (PA).

FIG. 3 shows a state in which end effector (200) is advanced distally relative to outer sheath (122), such that end effector (200) is distal to distal end (124) of outer sheath (122). In some versions, in order to transition between the state shown in FIG. 2 and the state shown in FIG. 3, inner shaft (150) remains longitudinally stationary relative to handle (110) while outer sheath (122) translates longitudinally relative to handle (110) and relative to inner shaft (150). In such versions, handle (110) or the proximal end of outer sheath (122) may include an actuator that may be manipulated by the physician (PH) to drive outer (122) sheath longitudinally relative to handle (110) and relative to inner shaft (150). As another merely illustrative variation, to transition between the state shown in FIG. 2 and the state shown in FIG. 3, outer sheath (122) remains longitudinally stationary relative to handle (110) while inner shaft (150) translates longitudinally relative to handle (110) and relative to outer sheath (122). In such versions, handle (110) may include an actuator that may be manipulated by the physician (PH) to drive inner shaft (150) longitudinally relative to handle (110) and relative to outer sheath (122).

FIG. 4 shows a state in which end effector (200) is in the distal position relative to outer sheath (122), but with panel assembly (210) in an outwardly splayed configuration, such that panel assembly (210) diverges away from the longitudinal axis (LA) of catheter (120). As shown in FIG. 4, end effector (200) presents a paddle-like or webbed hand configuration in this state. In comparing the configurations of panel assembly (210) in FIG. 3 to FIG. 4, when panel assembly (210) is in the collapsed or contracted state shown in FIG. 3, panel assembly (210) presents a profile having a lower surface area compared to when panel assembly (210) is in the outwardly splayed or expanded state shown in FIG. 4. Stated another way, end effector (200) includes panel assembly (210) that is movable from a first state to a second state, where a profile of panel assembly (210) has a higher surface area in the second state compared to the first state. In this manner, the surface area of the profile of panel assembly (210) is changeable from low to high. Merely illustrative examples of ways in which end effector may transition between the state shown in FIG. 3 and the state shown in FIG. 4 will be described in greater detail below; while other ways will be apparent to those skilled in the art in view of the teachings herein.

In the present example, panel assembly (210) includes a flexible circuit substrate (212), a plurality of spines (214), and a plurality of microelectrodes (216). In one version flexible circuit substrate (212) is made from a flexible polymer film laminated to a thin sheet of copper. This construction is etched on one or both sides to form a circuit pattern. This etched construction is coated with a polymer to provide insulation and sealing characteristics. Spines (214) extend along and attach with flexible circuit substrate (212). In the outwardly splayed configuration of FIG. 4, the combination of spines (214) and flexible circuit substrate (212) can be considered to have a webbed hand configuration or shape as mentioned above. In the collapsed or contracted configuration of FIG. 3, the combination of spines (214) and flexible circuit substrate (212) can be considered to have a cage-like configuration or shape. The illustrated configuration for spines (214) is merely exemplary, and other configurations for spines (214) usable with end effector (200) will be apparent to those skilled in the art in view of the teachings herein.

Microelectrodes (216) connect with spines (214) and in the present example are positioned along or between spines (214) in a longitudinally staggered configuration. Microelectrodes (216) are configured to sense potentials within tissue to detect aberrant electrical signals within tissue as mentioned above, such that microelectrodes (216) may be used to perform EP mapping. Flexible circuit substrate (212) connects with first driver module (14) via cable (30). Microelectrodes (216) are electrically connected with flexible circuit substrate (212) such that microelectrodes (216) can conduct the EP mapping.

In one version, microelectrodes (216) are electrically connected directly with flexible circuit substrate (212), for instance by soldering or by a conductive mechanical fastener. In another version, microelectrodes (216) are indirectly connected with flexible circuit substrate (212). In this indirect configuration, spines (214) are interconnected and at least one location of spines (214) electrically connects with flexible circuit substrate (212). Spines (214) then electrically connect with microelectrodes (216). In either approach, spines (214) are or can be covered by a non-conductive material to electrically isolate spines (214) from surrounding tissues and structures that spines (214) may contact.

As noted above and shown schematically in FIGS. 2-4, catheter assembly (100) is coupled with a guidance and drive system (10) via a cable (30). As discussed above, guidance and drive system (10) includes components and features that enable use of catheter assembly (100) in conducting EP mapping or RF ablation or both. Catheter assembly (100) is also coupled with a fluid source (42) via a fluid conduit (40). Fluid conduit (40) extends along the length of catheter (120) and is operable to deliver irrigation fluid (e.g., saline) out through distal end (124) of catheter. For instance, the fluid conduit may distally terminate at distal end (124). Alternatively, end effector (200) may incorporate one or more irrigation ports that are in communication with the fluid conduit. In either case, the irrigation fluid may provide cooling, flushing, or other effects at end effector (200) during operation of end effector (200) within the patient (PH). Various suitable ways in which catheter assembly (100) may provide irrigation will be apparent to those skilled in the art. Alternatively, some variations of catheter assembly (100) may lack irrigation capabilities, such that conduit (40), fluid source (42), and pump (44) may be omitted.

As also noted above and shown schematically in FIGS. 2-4, catheter assembly (100) of the present example further includes a pair of push-pull cables (160, 170) usable with catheter (120). Push-pull cables (160, 170) connect with a user input feature (190) configured to selectively deflect end effector (200) and a distal portion of catheter (120) laterally away from a longitudinal axis (LA) defined by a proximal portion of catheter (120) thereby enabling the physician (PH) to actively steer end effector (200) within the patient (PA). Various mechanisms that may be used for user input feature (190) to drive push-pull cables (160, 170) will be apparent to those skilled in the art in view of the teachings herein.

In addition to the foregoing, end effector (200) and other aspects of catheter assembly (100) may be configured and operable in accordance with at least some of the teachings of U.S. Pub. No. 2018/0056038, the disclosure of which is incorporated by reference herein in its entirety.

Figure 5:
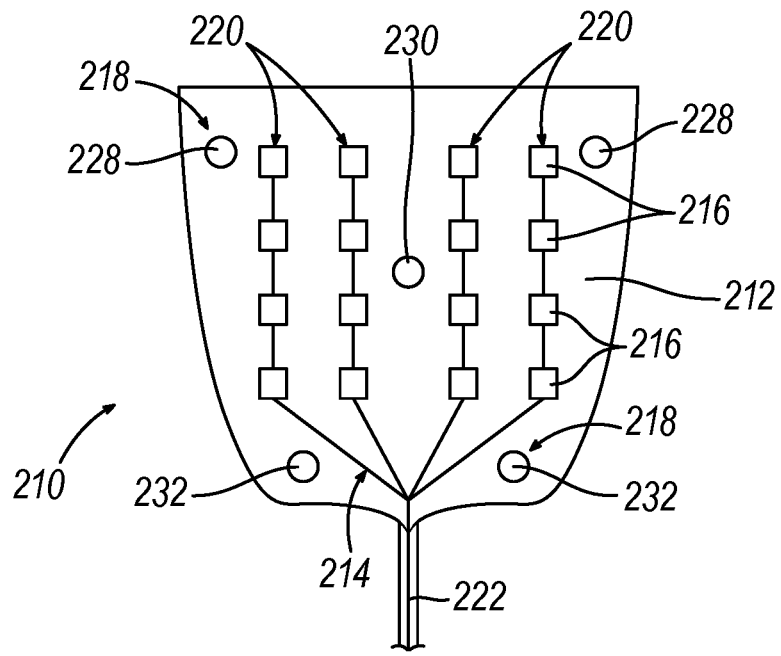
FIG. 5 depicts an enlarged perspective view of a panel assembly of the end effector of FIG. 2.

FIG. 5 depicts an enlarged view of panel assembly (210) of end effector (200) in its expanded state. Panel assembly (210) of this example includes flexible circuit substrate (212), spines (214), microelectrodes (216), and sensors (218). Flexible circuit substrate (212) of the present example is flexible and has a generally flat, planar configuration. By way of example only, flexible circuit substrate (212) may be formed of polyimide, polyether ether ketone, or any other suitable flex circuit substrate. A proximal end of flexible circuit substrate (212) is fixedly secured to inner shaft (150).

Flexible circuit substrate (212) of the present example includes multiple sections (220) of spines (214) with multiple microelectrodes (216). Sections (220) are shown in a linear arrangement or orientation with panel assembly (210) in its expanded state. At a proximal end of each section (220), spines (214) converge and join a control wire (222). In the present example control wire (222) connects with user input feature (190), but in other versions control wire (222) may be included with cable (30) and is connected with guidance and drive system (10). As will be described further below control wire (222) is configured for actuation to move panel assembly (210) from its contracted or collapsed state shown in FIGS. 2 and 3 to its expanded state shown in FIGS. 4 and 5.

In the present example, microelectrodes (216) are provided in pairs to provide bipolar sensing of potentials. The configuration of the pairs of microelectrodes (216) may be arranged longitudinally in some versions, and laterally in other versions. For instance, in one version longitudinally adjacent microelectrodes (216) make up the pair; while in another version laterally adjacent microelectrodes (216) make up the pair. Each pair of microelectrodes (216) is configured to provide bipolar sensing of electrocardiogram signals as the pair of electrodes (216) is placed in contact with cardiovascular tissue. Thus, a pair of microelectrodes (216) may be considered as collectively forming a single "sensor." Each microelectrode (216) may be coupled with a corresponding trace or other electrical conduit on flexible circuit substrate (212), thereby enabling signals picked up by microelectrodes (216) to be communicated back through electrical conduits (not shown) in catheter (120) to console (12), which may process the signals to provide EP mapping to thereby identify locations of aberrant electrical activity within the cardiac anatomy. This may in turn allow the physician (PH) to identify the most appropriate regions of cardiac tissue to ablate (e.g., with RF energy, cryoablation, etc.), to thereby prevent or at least reduce the communication of aberrant electrical activity across the cardiac tissue.

With the above described and illustrated arrangement, end effector (200) includes an array of microelectrodes (216). While microelectrodes (216) can be mounted to end effector (200) in a variety of ways, in the present version, the array of microelectrodes (216) are oriented in a matrix shape or arrangement. For instance, in the illustrated version a four by four matrix arrangement is shown, however other matrix arrangement can be used. In this manner, end effector (200) includes flexible circuit substrate (212) having a plurality of microelectrodes (216) contained in a defined surface area. The defined surface area being that surface area defined by the flexible circuit substrate (212) of end effector (200).

Configuring end effector (200) with this matrix of microelectrodes (216) where numerous microelectrodes (216) are contained in a defined surface area of end effector (200) allows catheter (120) with end effector (200) to evaluate electrograms or wave propagation in multiple orientations. In this way, during use of end effector (200), panel assembly (210) contacts the endocardium or epicardium such that multiple microelectrodes (216) are simultaneously in contact with this tissue. Having this large number of microelectrodes (216) in a defined surface area contacting tissue at the same time provides for the ability to detect and subsequently evaluate the direction of wave propagation. This information can provide the physician (PH) with greater information as to how electrical signals within the tissue of the patient (PA) are originating and traveling. This information can then be used to make ablation treatment decisions. In one example, catheter (120) with end effector (200) having the above-described configuration can be a diagnostic catheter for use in both ventricular tachycardia (VT) procedures as well as epicardial procedures.

As noted above, flexible circuit substrate (212) is flexible, such that flexible circuit substrate (212) may conform to the contours and other surface geometry of cardiac tissue when end effector (200) is pressed against cardiac tissue. The deformation of flexible circuit substrate (212) may promote full contact between two or more pairs of microelectrodes (216) and cardiac tissue. Such contact may be further promoted by providing a substantial number of microelectrodes (216) on flexible circuit substrate (212), as shown in FIGS. 4 and 5. In particular, microelectrodes (216) are provided along spines (214) of each section (220) in the present example. Having a substantial number of microelectrodes (216) enables end effector (200) to provide high density EP mapping through chambers of the heart (H), as several pairs of microelectrodes (216) can provide electrocardiogram signal sensing at multiple regions of cardiac tissue simultaneously.

The methods of contacting tissue with microelectrodes (216) of end effector (200) may vary based on the particular cardiovascular region in which the tissue is located. In some instances, a stamping motion may be used to create contact between tissue and microelectrodes (216) of end effector (200). By way of further example only, end effector (200) may engage tissue in accordance with any of the various techniques shown and described in U.S. Pat. No. 9,314,299, entitled "Flower Catheter for Mapping and Ablating Veinous and Other Tubular Locations," issued Apr. 19, 2016, the disclosure of which is incorporated by reference herein in its entirety. Other suitable ways in which microelectrodes (216) of end effector (200) may be brought into contact with tissue will be apparent to those skilled in the art in view of the teachings herein.

As shown in FIG. 4, microelectrodes (216) are positioned on an outer surface (224) of panel assembly (210) in this example. In addition, or in the alternative, microelectrodes (216) may be positioned on an inner surface (226) of panel assembly (210). For instance, in a version where microelectrodes (216) are positioned on both outer and inner surfaces (224, 226) of panel assembly (210), FIG. 5 depicts an exemplary arrangement of microelectrodes (216) as they would be positioned on each surface (224, 226) when panel assembly (210) is in the outwardly splayed or expanded configuration. It should also be understood that the positioning of microelectrodes (216) in the particular locations shown in FIGS. 4 and 5 is merely illustrative, and other positioning may be used in other versions. Accordingly, microelectrodes (216) may be provided in any other suitable number and arrangement along panel assembly (210) as will be apparent to those skilled in the art in view of the teachings herein. As another merely illustrative example, one or more ring electrodes (not shown) may be positioned on outer sheath (122), near distal end (124), to provide a reference signal during EP mapping to enable factoring out of far field signals. Similarly, one or more one or more ring electrodes (not shown) may be positioned on inner shaft (150) for providing a reference signal.

As yet another merely illustrative variation, ablation electrodes (not shown) may also be included on end effector (200). Ablation electrodes may be used to apply RF energy to tissue that is in contact with these ablation electrodes, to thereby ablate the tissue. Each ablation electrode may be coupled with a corresponding trace or other electrical conduit on flexible circuit substrate (212), thereby enabling console (12) to communicate RF energy through electrical conduits (not shown) in catheter (120) to the traces or other conduits on flexible circuit substrate (212) to reach the ablation electrodes. While multiple ablation electrodes may be incorporated into panel assembly (210) of end effector (200), it should be understood that in some scenarios, only one, only two, or some other relatively small number of ablation electrodes would be activated to apply RF energy to tissue at any given moment. The number and positioning of the ablation electrodes can vary and will be apparent to those skilled in the art in view of the teachings herein. Also, ablation electrodes may be absent or omitted entirely from end effector (200), leaving only microelectrodes (216) for EP mapping and diagnostic procedures.

By way of example only, microelectrodes (216) may be formed of platinum, gold, or any other suitable material. Microelectrodes (216) may include various coatings, if desired. For instance, microelectrodes (216) may include a coating that is selected to improve the signal-to-noise ratio of signals from microelectrodes (216). Such coatings may include, but need not be limited to, iridium oxide (IrOx) coating, poly(3,4-ethylenedioxythiophene) (PEDOT) coating, Electrodeposited Iridium Oxide (EIROF) coating, or any other suitable coating. Ablation electrodes, when present, may include a coating that is selected to prevent adherence of blood to the ablation electrodes. Various suitable kinds of coatings that may be used for either microelectrodes (216) or ablation electrodes will be apparent to those skilled in the art in view of the teachings herein.

Panel assembly (210) of the present example further includes sensors (218) some of which are position sensors (228). Each position sensor (228) is operable to generate signals that are indicative of the position and orientation of end effector (200) within the patient (PA). By way of example only, each position sensor (228) may be in the form of a wire coil or a plurality of wire coils (e.g., three orthogonal coils) that are configured to generate electrical signals in response to the presence of an alternating electromagnetic field generated by field generators (20). Each position sensor (228) may be coupled with a corresponding trace or other electrical conduit on flexible circuit substrate (212), thereby enabling signals generated by position sensors (228) to be communicated back through electrical conduits (not shown) in catheter (120) to console (12), which may process the signals to identify the position of end effector (200) within the patient (PA). Other components and techniques that may be used to generate real-time position data associated with end effector (200) may include wireless triangulation, acoustic tracking, optical tracking, inertial tracking, and the like.

The number and positioning of position sensors (228) is merely optional. For instance, some variations may just provide a single position sensor (228) at distal end, without any additional position sensors (228) being provided on panel assembly (210). In addition to including one or more position sensors (228) on panel assembly (210), a position sensor (228) may be incorporated into the distal end of inner shaft (150) or outer sheath (122), etc. Some variations of panel assembly (210) may lack a position sensor (228) altogether, regardless of whether a position sensor (228) is incorporated into the distal end of inner shaft (150) or outer sheath (122).

Sensors (218) also include one or more force sensors (230) configured to sense external forces that impinge against end effector (200). When end effector (200) encounters external forces (e.g., when end effector (200) is pressed against tissue), those external forces are communicated from end effector (200) to force sensor (230). A suitable signal corresponding to the magnitude and direction of the external force can be communicated from force sensor (230) back through electrical conduits (not shown) in catheter (120) to console (12), which may process the signals and inform the user of catheter (120) of exceeding a possible force threshold. In some other versions of catheter (120), force sensors (230) can be located on or within shaft (150) or outer sheath (122) instead or in addition to on panel assembly (210) of end effector (200).

Sensors (218) also include one or more temperature sensors (232) that can be in the form of a thermocouple, thermistor, or other suitable temperature sensor type. In versions where end effector (200) incorporates RF electrodes for ablation, temperature sensors (232) are configured to generate signals to communicate a temperature at or near an ablation site back through electrical conduits (not shown) in catheter (120) to console (12), which may process the signals and inform the user of catheter (120) of exceeding a possible temperature threshold. In some other versions of catheter (120), temperature sensors (232) can be located on or within shaft (150) or outer sheath (122) instead or in addition to on panel assembly (210) of end effector (200). In still other versions, temperature sensors (232) are omitted.

In the present example microelectrodes (216), and in some cases sensors (218), may be provided on flexible circuit substrate (212) as a thin film through a physical vapor deposition (PVD) process. Other methods may also be employed to provide microelectrodes (216), sensors (218), conductive traces, or other circuit components on flexible circuit substrate (212), including but not limited to sputter deposition, chemical vapor deposition (CVD), thermal deposition, etc.

While FIGS. 2-5 depict an exemplary configuration for panel assembly (210) of end effector (200), other suitable configurations for panel assembly (210) will be apparent to those skilled in the art in view of the teachings herein. By way of example only, panel assembly (210) may be flat, curved, spade-shaped, rectangular-shaped, leaf-shaped, or otherwise shaped. Also, by way of example only, panel assembly (210) in its expanded state shown in FIGS. 4 and 5 may be approximately 20 mm long. By way of further example only, panel assembly (210) may have a width ranging from approximately 11 mm to approximately 15 mm. Alternatively, panel assembly (210) may have any other suitable dimensions.

Figure 6:
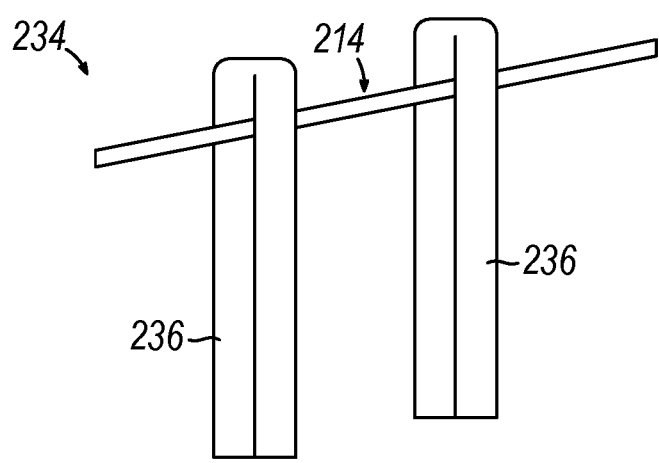
FIG. 6 depicts an enlarged perspective view of an exemplary weave option for forming a panel assembly of the end effector of FIG. 2.

As mentioned above, panel assembly (210) includes flexible circuit substrate (212), which may be constructed as a single layer or multiple layer film. Flexible circuit substrate may be constructed of various different kinds of materials, including but not limited to polyimide, liquid crystal polymer (LCP), or polyurethane. FIG. 6 depicts another option for construction of flexible circuit substrate (212) where flexible circuit substrate (212) is a woven structure (234). In this manner, threads (236) of material are woven together to form flexible circuit substrate (212). The materials used for threads (236) can include, for example, polyimide, polyether ether ketone, or any other suitable material for a flex circuit substrate. As shown in FIG. 6, spines (214) can be woven into the fabric making flexible circuit substrate (212). Similarly, cooper threads or cooper strips or sections can be incorporated to define portions of a circuit architecture. In some versions, a woven structure for flexible circuit substrate (212) can provide improved flexibility and thus ease of transitioning panel assembly (210) from its collapsed state of FIG. 3 to its expanded state of FIG. 4.

III. Exemplary End Effector Expansion and Contraction

As noted above with reference to the transition from the state shown in FIG. 3 to the state shown in FIG. 4, it may be desirable in some scenarios to transition end effector (200) between a state where panel assembly (210) is contracted to a state where panel assembly (210) is in an outwardly splayed configuration (e.g., resembling a paddle-like or webbed hand shape). By way of example only, it may be desirable to operate end effector (200) in an outwardly splayed configuration when end effector (200) is being used to perform EP mapping. To this extent, it may be desirable to incorporate control features into catheter assembly (100) to enable the physician (PH) to selectively control whether (or the extent to which) end effector (200) is in an outwardly splayed configuration or in a collapsed configuration. Merely illustrative examples of such control features are described in greater detail below, while other examples will be apparent to those skilled in the art in view of the teachings herein.

In one version, end effector (200) includes control wire (222) that is configured and operable to transition panel assembly (210) of end effector (200) from a collapsed or contracted state to an expanded state. For example, at the stage shown in FIG. 3, end effector (200) has been freed from the confines of outer sheath (122) with a proximal portion of panel assembly (210) connected with shaft (150). At this stage or state, panel assembly (210) of end effector (200) is in a collapsed configuration with spines (214) relaxed or not under tension. In the present example proximal ends of each spine (214) connect with control wire (222). In some versions, control wire (222) includes multiple wires joined together where each wire connects with a different respective proximal end of spines (214), while in other versions a control wire (222) includes a single wire that connects with each respective proximal end of spines (214). With either configuration, control wire (222) extends proximally through catheter (120) such that a proximal end of control wire (222) may be coupled with user input feature (190) that may include a slider, a rotary knob, or any other suitable actuator at handle (110) of catheter assembly (100). While the present example has control wire (222) connected with user input feature (190), in other versions control wire (222) may connect to another user input feature separate from user input feature (190).

When the physician (PH) wishes to transition from the collapsed configuration of FIG. 3 to the outwardly splayed configuration of FIG. 4, the physician (PH) actuates control wire (22) by manipulating user input feature (190) at handle (110) of catheter assembly (100). In response to this actuation of control wire (222), spines (214) are changed from a relaxed state not under tension to a state under tension. This tension in spines (214) cause spines (214) to assume the outwardly splayed configuration shown in FIGS. 4 and 5. This in turn spreads out flexible circuit substrate (212). In one version, actuation of control wire (222) retracts control wire (222) proximally such that control wire (222) pulls proximally on spines (214) thereby putting spines (214) under tension. In another version, control wire (222) can connect with distal ends of spines (214) and actuation of control wire (222) pushes spines (214) distally thereby putting spines (214) under tension to achieve the same or similar result of moving panel assembly (210) to its outwardly splayed configuration.

When the physician (PH) wishes to return end effector (200) back to the state shown in FIG. 3 from the state shown in FIG. 4, the physician (PH) may simply release control wire (222). With tension being relieved in control wires (222), spines (214) change to a neutral or relaxed state not under tension. In one example, spines (214) are formed with a shape memory material, e.g. nitinol, where spines (214)— when in a neutral or relaxed state—adopt a closely positioned configuration such as that shown in FIG. 3. In another example, spines (214) may include moveable joints where segments of spines (214) connect or where spines (214) connect with microelectrodes (216). When in the neutral or relaxed state, these joints allow spines (214) to move, including collapsing to the configuration shown in FIG. 3. After reaching this contracted or collapsed state for panel assembly (210), the physician (PH) may return end effector (200) to the interior of outer sheath (122) (e.g., by retracting end effector (200) proximally relative to outer sheath (122) or by advancing outer sheath (122) distally relative end effector (200)), then withdraw catheter (120) from the patient (PA).

To facilitate selective retraction of control wire (222), handle (110) of catheter assembly (100) may include one or more visual indicators, tactile detent features, or other user feedback features that may be associated with the user input device that drives translation of control wire (222). Such user feedback features may enable the physician (PH) to more easily control and determine the extent to which panel assembly (210) has achieved its fully outwardly splayed position or configuration, thereby enabling the physician (PH) to more easily control and determine the configuration of end effector (200).

In another version, spines (214) are attached with flexible circuit substrate (212) in a manner where spines (214) are resiliently biased to adopt a spread-out configuration as shown in FIGS. 4 and 5. For instance, spines (214) may be constructed of nitinol or another shape memory material with spines (214) configured to adopt the outwardly splayed state of FIGS. 4 and 5. Despite spines (214) being biased to this configuration, panel assembly (210) remains flexible enough to compress within outer sheath as shown in FIG. 2. In some variations, this resilience is instead or in addition provided by the material forming flexible circuit substrate (212). In some other variations, one or more resilient features (not shown) are added to flexible circuit substrate (212) or spines (214) to impart the resilient bias. By way of example only, one or more nitinol strips or other nitinol structures may be applied to flexible circuit substrate (212). Such nitinol strips may be applied using the vapor deposition process or other manufacturing techniques noted above. In versions where microelectrodes (216) are provided on outer surface (224) and inner surface (226) of panel assembly (210), the nitinol strips or other resilient members may be interposed between layers of the flexible material (e.g., polyimide, polyether ether ketone, etc.) forming flexible circuit substrate (212). Alternatively, the nitinol strips or other resilient members may be positioned along regions of flexible circuit substrate (212) where microelectrodes (216) are not present.

In addition to providing a resilient bias toward the expanded configuration shown in FIG. 4, resiliently biased spines (214) may also bias panel assembly (210) toward having a flat or paddle-like or webbed hand configuration. Of course, in other versions this bias can impart a curved configuration, or any other suitable configuration. As yet another merely illustrative example, in versions where nitinol is incorporated into spines (214) or other components of panel assembly (210), the nitinol may be shape-set to expand at human body temperature.

In one version where spines (214) are resiliently biased to the outwardly splayed configuration, control wire (222) connects with spine (214) and can apply tension to spines (214) via user input feature (190) as described above. In applying this tension to spines (214) in this example, spines (214) cause panel assembly (210) to adopt a collapsed or compact cylindrical configuration or shape, e.g. similar to that shown in FIG. 3. In still another version, resiliently biased spines (214) can be biased to multiple positions with one position being collapsed to a cylindrical configuration or shape, and with another position being expanded to the outwardly splayed configuration. In this example, actuation of control wire (222) can be used to change the biased state of spines (214) and thus the state or configuration of panel assembly (210).

In another variation of this example, control wire (222) may not be needed to alter the configuration and instead the physician (PH) may cause panel assembly (210) to contact tissue or a structure within patient (PA) to move spines (214) from one biased state or position to the other. By way of example only, pushing outer surface (224) against a structure may cause panel assembly (210) to adopt the outwardly splayed position or configuration shown in FIG. 4, while pushing inner surface (226) against a structure may cause panel assembly (210) to adopt the collapsed or contracted state shown in FIG. 3. While the foregoing examples include various ways to transition end effector (200) from the state shown in FIG. 3 to the state shown in FIG. 4, various other suitable structures and techniques may be used to provide a similar transition as will be apparent to those of skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprises a catheter assembly having a proximal end and a distal end, the catheter assembly defining a longitudinal axis, and the catheter assembly including an outer sheath with a distal end. The apparatus further comprises an end effector associated with the distal end of the catheter assembly, the end effector comprising a panel assembly, the panel assembly configured to transition between a first state and a second state. The panel assembly is configured to fit within the outer sheath in the first state, and configured to expand outwardly away from the longitudinal axis in the second state when exposed distally relative to the distal end of the outer sheath. The panel assembly comprises a flexible circuit substrate, a plurality of spines extending along the flexible circuit substrate, and a plurality of microelectrodes positioned along the plurality of spines.

Example 2

The apparatus of Example 1, the outer sheath being operable to translate relative to the end effector between a first longitudinal position and a second longitudinal position, the outer sheath being configured to contain the end effector in the first longitudinal position, the outer sheath being configured to expose the end effector in the second longitudinal position.

Example 3

The apparatus of Example 1, the end effector being operable to translate relative to the outer sheath between a first longitudinal position and a second longitudinal position, the end effector being configured to be contained in the outer sheath in the first longitudinal position, the end effector being configured to be exposed from the outer sheath in the second longitudinal position.

Example 4

The apparatus of any one or more of Example 1 through Example 3, the spines being expandable outwardly away from the longitudinal axis in the second state when exposed distally relative to the distal end of the outer sheath.

Example 5

The apparatus of any one or more of Example 1 through Example 4, the panel assembly further comprising at least one control wire, the at least one control wire operable to transition the panel assembly from the first state to the second state.

Example 6

The apparatus of Example 5, the plurality of spines extending distally from the at least one control wire.

Example 7

The apparatus of any one or more of Example 5 through Example 6, the at least one control wire operable to expand the panel assembly such that the panel assembly adopts a flat, planar configuration in the second state.

Example 8

The apparatus of any one or more of Example 5 through Example 7, the at least one control wire operable to contract the panel assembly to thereby cause the panel assembly to collapse inwardly toward the longitudinal axis.

Example 9

The apparatus of Example 7, the at least one control wire being configured to cause the plurality of spines to deflect outward from the longitudinal axis such that the panel assembly adopts the flat, planar configuration of the second state in response to adding tension to the at least one control wire.

Example 10

The apparatus of Example 8, the at least one control wire being configured to cause the plurality of spines to move inward toward the longitudinal axis such that the panel assembly adopts a cylindraceous configuration of the first state in response to removing tension from the at least one control wire.

Example 11

The apparatus of any one or more of Example 1 through Example 10, the panel assembly defining a profile, the profile having a first surface area in the first state and a second surface area in the second state, the surface area in the second state being larger than the surface area in the first state.

Example 12

The apparatus of any one or more of Example 1 through Example 11, the plurality of microelectrodes being arranged in a matrix configuration.

Example 13

The apparatus of any one or more of Example 1 through Example 12, the microelectrodes comprising at least one pair of bipolar sensing microelectrodes configured to sense potentials in tissue.

Example 14

The apparatus of any one or more of Example 1 through Example 13, further comprising a position sensor, the position sensor being operable to generate a signal indicative of a position of one or both of at least a portion of the catheter shaft assembly or at least a portion of the end effector in three-dimensional space.

Example 15

The apparatus of claim 14, the position sensor being located on a portion of the panel assembly.

Example 16

The apparatus of any one or more of Example 1 through Example 3, the spines being resiliently biased to expand outwardly away from the longitudinal axis in the second state when exposed distally relative to the distal end of the outer sheath.

Example 17

The apparatus of any one or more of Example 1 through Example 16, the spines comprising nitinol.

Example 18

The apparatus of any one or more of Example 1 through Example 17, the spines comprising a shape memory material.

Example 19

The apparatus of Example 18, the shape memory material comprising a temperature sensitive material, such that the shape memory material is configured to transition from a first shape to a second shape in response to a change in temperature.

Example 20

An apparatus for performing electrophysiological mapping comprises a catheter assembly having a proximal end and a distal end, the catheter assembly defining a longitudinal axis, the catheter assembly including an outer sheath with a distal end. The apparatus further comprises an end effector associated with the distal end of the catheter assembly, the end effector comprising a panel assembly comprising: a flexible circuit substrate, a plurality of spines extending along the flexible circuit substrate, and a plurality of microelectrodes positioned along the plurality of spines and configured to sense potentials in tissue. The end effector being operable to transition between a first state, a second state, and a third state, the panel assembly being configured to fit within the outer sheath in the first state, the panel assembly being configured to extend distally from the distal end of the outer sheath in the second state with the panel assembly collapsed inwardly toward the longitudinal axis, and the panel assembly being configured to adopt a flat, planar configuration in the third state.

Example 21

A method comprises (a) actuating a user input feature of a catheter assembly to transition an end effector from a first state to a second state, the catheter assembly including an outer sheath, the end effector comprising a panel assembly including an array of microelectrodes arranged in a matrix and configured for electrophysiological mapping, the panel assembly being contained in the outer sheath in the first state, the panel assembly being exposed relative to the outer sheath in the second state with the panel assembly expanded outwardly away from a longitudinal axis defined by the catheter assembly in the second state. The method further comprises (b) actuating the end effector to transition from the second state to the first state, the panel assembly returning to within the outer sheath in the first state.

V. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus comprising:
   (a) a catheter assembly having a proximal end and a distal end, the catheter assembly defining a longitudinal axis, the catheter assembly including an outer sheath with a distal end; and
   (b) an end effector associated with the distal end of the catheter assembly, the end effector comprising a panel assembly, the panel assembly being configured to transition between a confined state and an expanded state, the panel assembly being configured to fit within the outer sheath in the confined state, the panel assembly being configured to expand outwardly away from the longitudinal axis into a generally planar configuration in the expanded state when exposed distally relative to the distal end of the outer sheath, the panel assembly comprising:
      (i) a common flexible circuit substrate,
      (ii) a plurality of spines extending along and attached to the common flexible circuit substrate, the plurality of spines being connected to each other at their proximal ends and unconnected from each other at their distal ends,
      (iii) a plurality of microelectrodes positioned along the plurality of spines, and
      (iv) at least one control wire attached to the plurality of spines, the plurality of spines being connected to each other at their proximal ends via the at least one control wire, the at least one control wire being configured to adjust tension in the plurality of spines such that the plurality of spines actuate the panel assembly between the confined state and the expanded state.

2. The apparatus of claim 1, the outer sheath being operable to translate relative to the end effector between a first longitudinal position and a second longitudinal position, the outer sheath being configured to contain the end effector in the first longitudinal position, the outer sheath being configured to expose the end effector in the second longitudinal position.

3. The apparatus of claim 1, the end effector being operable to translate relative to the outer sheath between a first longitudinal position and a second longitudinal position, the end effector being configured to be contained in the outer sheath in the first longitudinal position, the end effector being configured to be exposed from the outer sheath in the second longitudinal position.

4. The apparatus of claim 1, the plurality of spines being expandable outwardly away from the longitudinal axis in the expanded state when exposed distally relative to the distal end of the outer sheath.

5. The apparatus of claim 1, the plurality of spines extending distally from the at least one control wire.

6. The apparatus of claim 1, the at least one control wire operable to expand the panel assembly such that the panel assembly adopts the generally planar configuration in the expanded state.

7. The apparatus of claim 6, the at least one control wire being configured to cause the plurality of spines to deflect outward from the longitudinal axis such that the panel assembly adopts the generally planar configuration of the expanded state in response to adding the tension to the at least one control wire.

8. The apparatus of claim 1, the at least one control wire operable to contract the panel assembly to thereby cause the panel assembly to collapse inwardly toward the longitudinal axis to adopt a collapsed state.

9. The apparatus of claim 8, the at least one control wire being configured to cause the plurality of spines to move inward toward the longitudinal axis such that the panel assembly adopts a cylindraceous configuration of the collapsed state in response to removing the tension from the at least one control wire.

10. The apparatus of claim 1, the panel assembly defining a profile, the profile having a first surface area in the collapsed state and a second surface area in the expanded state, the surface area in the expanded state being larger than the surface area in the collapsed state.

11. The apparatus of claim 1, the plurality of microelectrodes being arranged in a matrix configuration.

12. The apparatus of claim 1, the plurality of microelectrodes comprising at least one pair of bipolar sensing microelectrodes configured to sense potentials in tissue.

13. The apparatus of claim 1, further comprising a position sensor, the position sensor being operable to generate a signal indicative of a position of one or both of at least a portion of the catheter assembly or at least a portion of the end effector in three-dimensional space.

14. The apparatus of claim 13, the position sensor being located on a portion of the panel assembly.

15. The apparatus of claim 1, the plurality of spines being resiliently biased to expand outwardly away from the longitudinal axis in the expanded state when exposed distally relative to the distal end of the outer sheath.

16. The apparatus of claim 1, the plurality of spines comprising a shape memory material.

17. The apparatus of claim 16, the shape memory material comprising a temperature sensitive material, such that the shape memory material is configured to transition from a first shape to a second shape in response to a change in temperature.

18. An apparatus for performing electrophysiological mapping comprising:
   (a) a catheter assembly having a proximal end and a distal end, the catheter assembly defining a longitudinal axis, the catheter assembly including an outer sheath with a distal end; and
   (b) an end effector associated with the distal end of the catheter assembly, the end effector comprising a panel assembly comprising:
      (i) a common flexible circuit substrate,
      (ii) a plurality of spines extending along and attached to the common flexible circuit substrate, the plurality of spines being connected to each other at their proximal ends and unconnected from each other at their distalmost ends,
      (iii) a plurality of microelectrodes positioned along the plurality of spines and configured to sense potentials in tissue, and
      (iv) a control wire attached to the plurality of spines, the plurality of spines being connected to each other at their proximal ends via the control wire, the control wire being configured to adjust a tension within the plurality of spines to thereby flex the common flexible circuit substrate,
   the end effector being operable to transition between a first state, a second state, and a third state,
   the panel assembly being configured to fit within the outer sheath in the first state,
   the panel assembly being configured to extend distally from the distal end of the outer sheath in the second state with the panel assembly collapsed inwardly toward the longitudinal axis, and
   the panel assembly being configured to adopt a flat, planar configuration in the third state.

19. A method comprising:
(a) actuating a user input feature of a catheter assembly to transition an end effector of the catheter assembly from a first state to a second state, the catheter assembly including an outer sheath, the end effector comprising a panel assembly including an array of microelectrodes arranged in a matrix and configured for electrophysiological mapping, the panel assembly including a common flexible substrate attached to the microelectrodes and a plurality of spines attached to and extending along the common flexible substrate, the plurality of spines being connected to each other at their proximal ends and unconnected from each other at their distalmost ends, the panel assembly being contained in the outer sheath in the first state, the panel assembly being exposed relative to the outer sheath in the second state with the panel assembly expanded outwardly away from a longitudinal axis defined by the catheter assembly in the second state; and
(b) actuating the end effector to transition from the second state to the first state by adjusting a tension value of the plurality of spines such that the plurality of spines flexes the common flexible substrate, the panel assembly returning to within the outer sheath in the first state.

* * * * *